US011227392B2

(12) United States Patent
Halmann

(10) Patent No.: US 11,227,392 B2
(45) Date of Patent: Jan. 18, 2022

(54) ULTRASOUND IMAGING SYSTEM AND METHOD

(71) Applicant: GE Precision Healthcare LLC, Wauwatosa, WI (US)

(72) Inventor: Menachem Halmann, Monona, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 152 days.

(21) Appl. No.: 16/870,633

(22) Filed: May 8, 2020

(65) Prior Publication Data
US 2021/0350539 A1    Nov. 11, 2021

(51) Int. Cl.
*G06K 9/00* (2006.01)
*G06T 7/00* (2017.01)
*A61B 8/00* (2006.01)
*G06T 3/40* (2006.01)

(52) U.S. Cl.
CPC ............. *G06T 7/0016* (2013.01); *A61B 8/42* (2013.01); *A61B 8/4488* (2013.01); *A61B 8/461* (2013.01); *G06T 3/4007* (2013.01); *G06T 2207/10016* (2013.01); *G06T 2207/10132* (2013.01); *G06T 2207/30061* (2013.01)

(58) Field of Classification Search
CPC ................. G06T 7/0016; G06T 3/4007; G06T 2207/10016; G06T 2207/10132; G06T 2207/30061; A61B 8/42; A61B 8/4488; A61B 8/461
See application file for complete search history.

(56) References Cited

U.S. PATENT DOCUMENTS

| | | | |
|---|---|---|---|
| 6,674,879 B1 * | 1/2004 | Weisman | A61B 8/06 378/94 |
| 8,002,704 B2 | 8/2011 | Torp | |
| 10,192,032 B2 | 1/2019 | Himsl | |
| 2006/0251306 A1 * | 11/2006 | Shin | G06T 7/262 382/128 |
| 2009/0306514 A1 | 12/2009 | Imamura | |
| 2014/0031688 A1 | 1/2014 | Perrey | |
| 2015/0116361 A1 | 4/2015 | Braun | |
| 2016/0335742 A1 * | 11/2016 | Yim | A61B 8/5253 |
| 2017/0000462 A1 * | 1/2017 | Washburn | A61B 8/0891 |

(Continued)

OTHER PUBLICATIONS

Jing Jin; Xuemeng Li; Yan Wang; Qi Wang; Yi Shen, "Panoramic imaging of ultrasound videos based on multi-mixing measures", 2010 IEEE International Conference on Imaging Systems and Techniques, Date of Conference: Jul. 1-2, 2010 (Year: 2010).*

(Continued)

*Primary Examiner* — Atiba O Fitzpatrick

(57) ABSTRACT

An ultrasound imaging system and method includes acquiring ultrasound image data while moving an ultrasound probe, automatically identifying a plurality of segments of interest in the ultrasound image data, automatically applying temporal scaling to at least one of the plurality of segments of interest, and displaying the ultrasound image data as a panoramic view comprising a plurality of videos, where each of the plurality of videos is based on a different one of the plurality of the segments of interest, and where, based on the temporal scaling, each of the plurality of videos in the panoramic view takes the same amount of time to play.

20 Claims, 8 Drawing Sheets

(56) References Cited

U.S. PATENT DOCUMENTS

2018/0310920 A1 11/2018 Specht
2019/0125298 A1 5/2019 Abolmaesumi
2019/0328361 A1 10/2019 Halmann

OTHER PUBLICATIONS

Yipeng Liu; Jing Jin; Qiang Wang; Shen Yi, "Ultrasound extended-field-of-view imaging based on motion estimation using quaternion wavelet", 2012 IEEE International Instrumentation and Measurement Technology Conference Proceedings, Date of Conference: May 13-16, 2012 (Year: 2012).*
M. Paterni; F. Faita; A. Benassi; M. Demi, "Synthesis of panoramic views of peripheral vessels from sequences of echographic images", Computers in Cardiology, 2003, Date of Conference: Sep. 21-24, 2003 (Year: 2003).*
Yasameen Al Youzbaki; Silviu Stanciu; Sever Paşca, "Creating panoramic image for linear transducer ultrasound Doppler images", 2015 E-Health and Bioengineering Conference (EHB), Date of Conference: Nov. 19-21, 2015 (Year: 2015).*
"Confidence-Driven Control of an Ultrasound Probe" Pierre Chatelain, Alexandre Krupa, Nassir Navab. Confidence-Driven Control of an Ultrasound Probe. IEEE Transactions on Robotics, Institute of Electrical and Electronics Engineers (IEEE), 2017, 33 (6), pp. 1410-1424. hal-01551431.

* cited by examiner

ULTRASOUND IMAGING SYSTEM AND METHOD

FIELD OF THE INVENTION

The subject matter disclosed herein relates generally to ultrasound imaging systems and methods of ultrasound imaging.

BACKGROUND OF THE INVENTION

Ultrasound imaging is an imaging modality capable of acquiring ultrasound image data that may be viewed in real-time or stored and reviewed at times subsequent to the acquisition. Ultrasound imaging systems also have the ability to acquire and store one or more videos, each including a plurality of image frames acquired at different points in time. Displaying ultrasound image data as videos allows the clinician to see how a person's anatomy changes over time. The size of the field-of-view (FOV) of an ultrasound probe used with the ultrasound imaging system dictates the maximum area or the maximum volume that may be acquired in a single frame of ultrasound data. A clinician operating the ultrasound imaging system may miss one or more items of interest during an ultrasound examination due to the size of the FOV, especially when trying to examine large organs or large regions of the person's body.

In order to minimize the likelihood of missing one or more items of interest in the ultrasound image data, particularly when imaging organs that are relatively large in comparison to the FOV, some conventional ultrasound imaging system are configured to generate panoramic views. A panoramic view may be generated from multiple ultrasound images acquired at different spatial locations. The ultrasound images may be combined or stitched together in order to provide a single panoramic view that covers a larger area or volume than would be possible with a single ultrasound image due to constraints imposed by the size of the FOV.

The ultrasound images used to generate a panoramic view may either be still frames, each representing a person's anatomy at a single point in time, or each of the ultrasound images in the panoramic view may be a video. For embodiments where each of the ultrasound images in the panoramic view is a video, there are challenges to displaying the videos in a way that is easy to interpret for the clinician. Since each of the individual videos was acquired at a different time, various patient vitals, such as heartrate or respiratory rate may be different between the various videos. It is known to temporally synchronize the individual videos based on a parameter such as respiratory rate or heartrate. However, this does not address a fundamental issue when displaying ultrasound images as videos in a panoramic view. Each of the videos may be displayed as a repeating loop so that it plays continuously. This means that each of the videos may have a different period. When a plurality of different video loops, each with a different period, are combined into a panoramic view and played at the same time, the result can be visually confusing for the clinician. The mismatch between the various video loops can be distracting for the clinician. The visual changes due to the mismatch between video lengths may attract the clinician's attention, making it harder to identify clinically important features in the videos. As such, there is a need for an improved ultrasound imaging system and method of ultrasound imaging where the videos in the panoramic view are automatically temporally scaled so that all of them take the same amount of time to play.

BRIEF DESCRIPTION OF THE INVENTION

In one embodiment, a method of ultrasound imaging includes acquiring ultrasound image data while moving an ultrasound probe. The method includes automatically identifying a plurality of segments of interest in the ultrasound data. The method includes automatically applying temporal scaling to at least one of the plurality of segments of interest. The method includes displaying the ultrasound image data as a panoramic view comprising a plurality of videos, wherein each of the plurality of videos is based on a different one of the plurality of segments of interest, and wherein, based on the temporal scaling, each of the plurality of videos in the panoramic view takes the same amount of time to play.

In one embodiment, an ultrasound imaging system includes a display device, an ultrasound probe configured to acquire ultrasound image data, and a processor in electronic communication with the ultrasound probe and the display device. The processor is configured to automatically identify a plurality of segments of interest in the ultrasound image data and to automatically apply temporal scaling to at least one of the plurality of segments of interest. The processor is configured to display, on the display device, the ultrasound image data as a panoramic view comprising a plurality of videos, wherein each of the plurality of videos is based on a different one of the plurality of segments of interest, and wherein, based on the temporal scaling, each of the plurality of videos in the panoramic view takes the same amount of time to play.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION OF THE INVENTION

At least one technical effect of the inventive subject matter described herein includes displaying a plurality of segments of interest as a panoramic view including a plurality of videos, where each of the plurality of videos in the panoramic view takes a same amount of time to play based on temporal scaling applied to at least one of the plurality of segments of interest.

Figure 1:
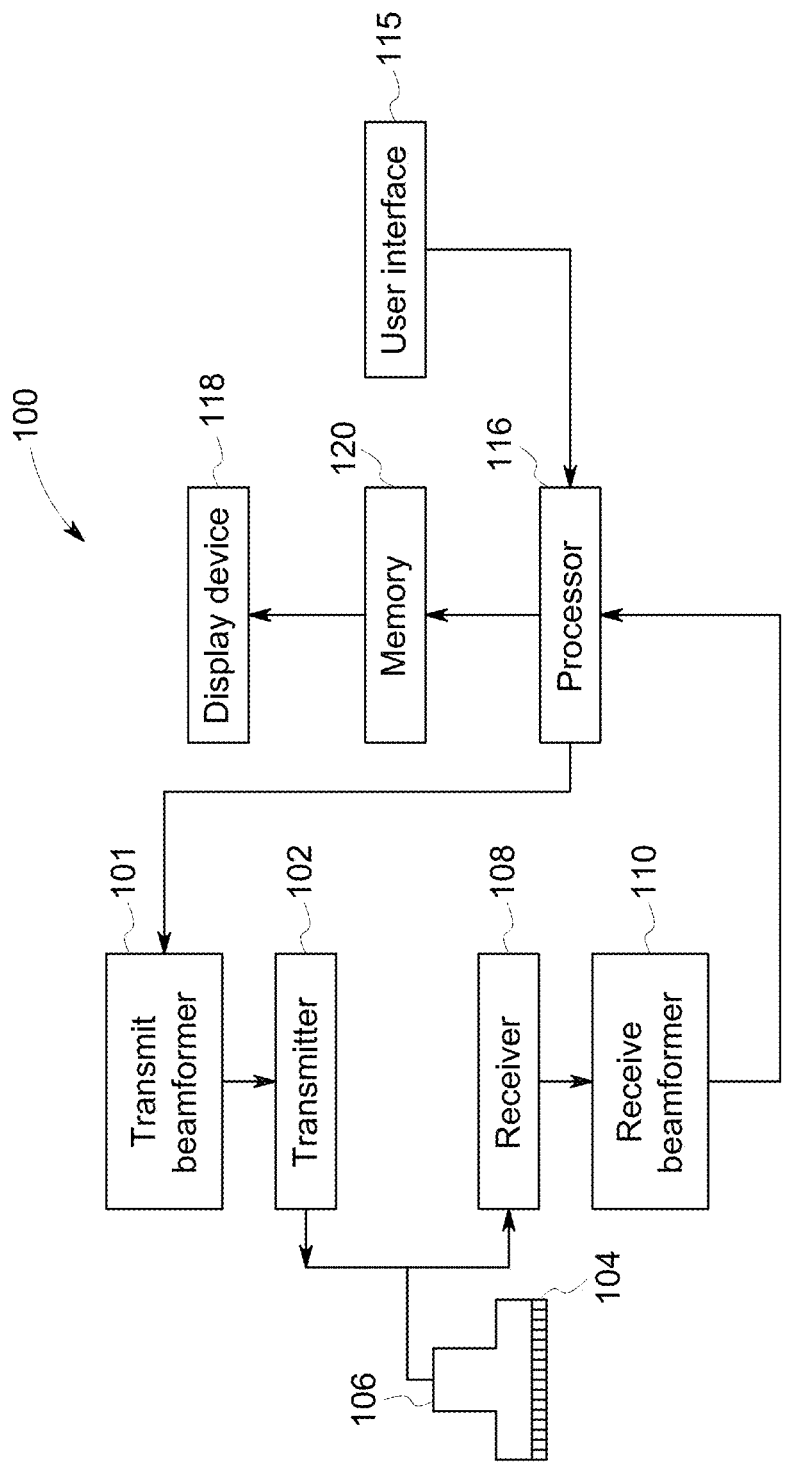
FIG. 1 is a schematic diagram of an ultrasound imaging system in accordance with an embodiment.

FIG. 1 is a schematic diagram of an ultrasound imaging system 100 in accordance with one embodiment of the inventive subject matter described herein. The ultrasound imaging system 100 includes a transmit beamformer 101 and a transmitter 102 that drive elements 104 within an ultrasound probe 106 to emit pulsed ultrasonic signals into a body (not shown). According to an embodiment, the ultrasound probe 106 may be a linear probe, a curvilinear probe, a phased array probe, a linear phased array probe, a curvilinear phased array probe, a two-dimensional matrix array probe, a curved two-dimensional matrix array probe, a mechanical 3D probe, or any other type of ultrasound probe capable of acquiring diagnostic ultrasound images.

The pulsed ultrasonic signals are back-scattered from structures in the body, such as blood cells or muscular tissue, to produce echoes that return to the elements 104. The echoes are converted into electrical signals by the elements 104, and the electrical signals are received by a receiver 108. The electrical signals representing the received echoes are passed through a receive beamformer 110 that outputs ultrasound image data. The ultrasound probe 106 may contain electronic circuitry to do all or part of the transmit and/or the receive beamforming. For example, all or part of the transmit beamformer 101, the transmitter 102, the receiver 108, and the receive beamformer 110 may be situated within the ultrasound probe 106 in other embodiments. Scanning may include acquiring data through the process of transmitting and receiving ultrasonic signals. Ultrasound image data acquired by the ultrasound probe 106 can include one or more datasets acquired with the ultrasound imaging system 100. A user interface 115 may be used to control operation of the ultrasound imaging system 100, including, to control the input of data, to change a scanning or display parameter, and the like. The user interface may include, for instance, one or more of a touchscreen, a keyboard, a touch pad, a track ball, a mouse, one or more rotary knobs, one or more hard keys, and one or more soft keys.

The ultrasound imaging system 100 also includes a processor 116 that controls the transmit beamformer 101, the transmitter 102, the receiver 108, and the receive beamformer 110. The processor 116 is in electronic communication with the probe 106 via one or more wired and/or wireless connections. The processor 116 may control the ultrasound probe 106 to acquire data. The processor 116 controls which of the elements 104 are active and the shape of a beam emitted from the ultrasound probe 106. The processor 116 is also in electronic communication with a display device 118, and the processor 116 may process the data into images for display on the display device 118. The processor 116 may include one or more central processors according to an embodiment. According to other embodiments, the processor 116 may include one or more other electronic components capable of carrying out processing functions, such as one or more digital signal processors, field-programmable gate arrays, graphic boards, and/or integrated circuits. According to other embodiments, the processor 116 may include multiple electronic components capable of carrying out processing functions. Other embodiments may use two or more separate processors to perform the functions performed by the processor 116 according to the exemplary embodiment shown in FIG. 1. According to another embodiment, the processor 116 may also include a complex demodulator (not shown) that demodulates the radio frequency data and generates raw data. In another embodiment, the demodulation can be carried out earlier in the processing chain.

The processor 116 is adapted to perform one or more processing operations according to a plurality of selectable ultrasound modalities on the data. The data may be processed in real-time during a scanning session as the echo signals are received, such as by processing the data without any intentional delay, or processing the data while additional data is being acquired during the same imaging session of the same person.

The data may be stored temporarily in a buffer (not shown) during a scanning session and processed in less than real-time in a live or off-line operation. Some embodiments of the inventive subject matter may include multiple processors (not shown) to handle the processing tasks that are handled by the processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire ultrasound data at a frame-rate of, for example, 10 to 30 hertz. Images generated from the data may be refreshed at a similar frame-rate. Other embodiments may acquire and display ultrasound data at different rates. For example, some embodiments may acquire ultrasound data at a frame-rate of less than 10 hertz or greater than 30 hertz.

A memory 120 is included for storing processed frames of acquired data. In one embodiment, the memory 120 is of sufficient capacity to store at least several seconds worth of ultrasound image data. The frames of data are stored in a manner to facilitate retrieval thereof according to their order or time of acquisition. The memory 120 may comprise any known data storage medium, such as one or more tangible and non-transitory computer-readable storage media (e.g., one or more computer hard drives, disk drives, universal serial bus drives, solid-state drives, or the like).

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form two- or three-dimensional image data. For example, one or more modules may generate B-mode, color Doppler, M-mode, color M-mode, spectral Doppler, Elastography, TVI, strain, strain rate and combinations thereof, and the like. Timing information indicating a time at which the data was acquired in memory may be recorded. The modules may include, for example, a scan conversion module to perform scan conversion operations to convert the image volumes from beam space coordinates to display space coordinates. A video processor module may read the image frames from a memory and displays an image in real time while a procedure is being carried out on a person. A video processor module may store the images in an image memory, from which the images are read and displayed.

Figure 2:
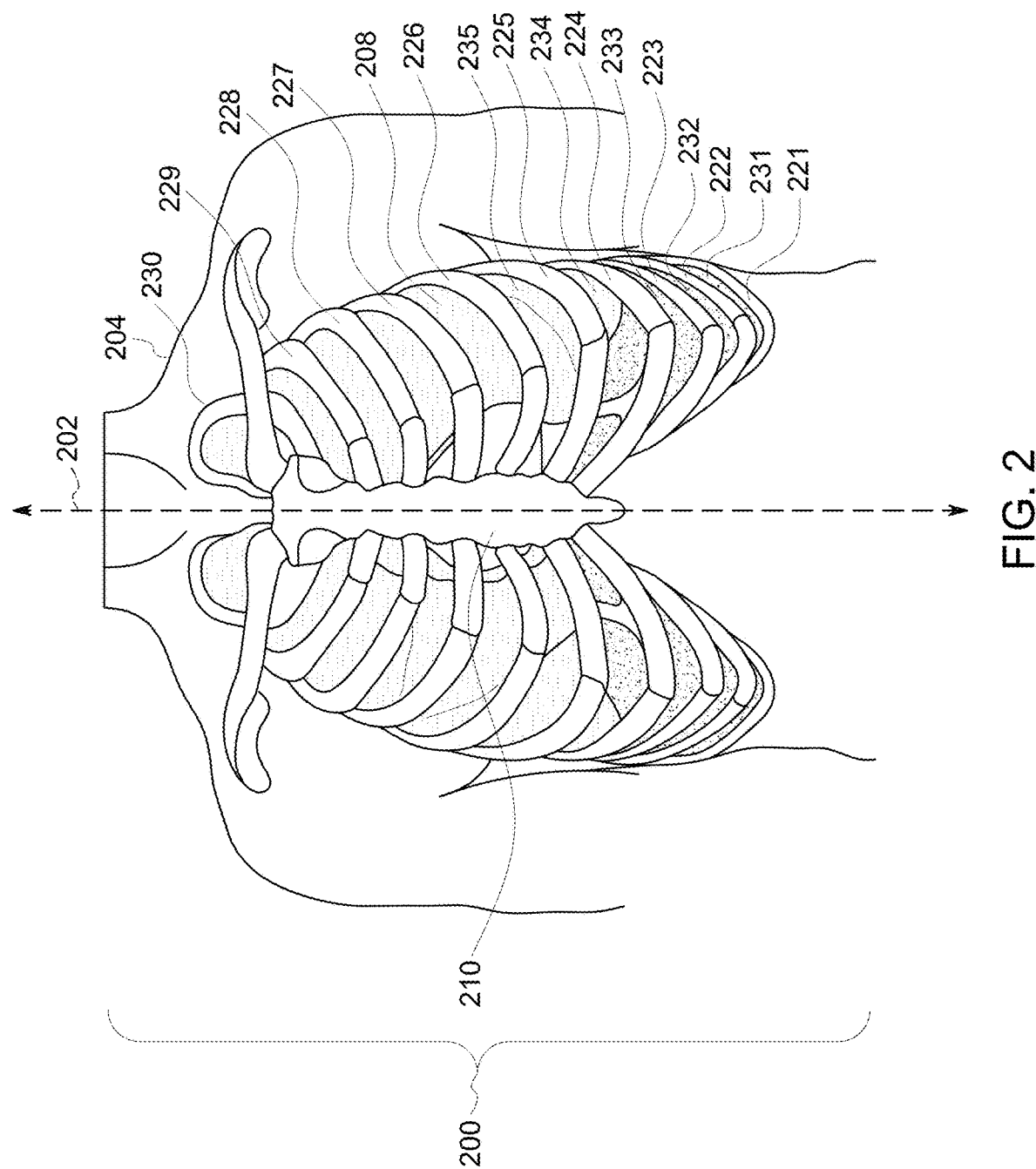
FIG. 2 illustrates a thoracic cavity according to an example.

FIG. 2 illustrates a thoracic cavity 200 of a person 204 according to one example. The ultrasound image data that is acquired (as described herein) may represent portions of the thoracic cavity 200, including lungs 208, a plurality of ribs, and a sternum 210 of the person 204. The plurality of ribs may include a first rib 221, a second rib 222, a third rib 223, a fourth rib 224, a fifth rib 225, a sixth rib 226, a seventh rib 227, an eighth rib 228, a ninth rib 229, and a tenth rib 230. FIG. 2 also shows a plurality of intercostal spaces located between the ribs. For instance, a first intercostal space 231, a second intercostal space 232, a third intercostal space 233, a fourth intercostal space 234, and a fifth intercostal space 235 are all represented in FIG. 2. The first intercostal space 231 is located between the first rib 221 and the second rib 222; the second intercostal space 232 is located between the second rib 222 and the third rib 223; the third intercostal space 233 is located between the third rib 223 and the fourth rib 224; and the fourth intercostal space 234 is located between the fourth rib 224 and the fifth rib 225. The thoracic cavity 200 of the person 204 includes additional intercostal spaces; however, these additional intercostal spaces have not been specifically identified on FIG. 2. In obtaining the ultrasound image data, the ultrasound probe 106 shown in FIG. 1 may be held in contact with an exterior surface of the skin of the person 204 and moved longitudinally along the person 204 (e.g., in a direction that is closer to parallel to the length or height of the person 204 than one or more other directions). This movement also causes the ultrasound probe 106 to move transversely relative to the plurality of ribs. For example, the ultrasound probe 106 may be moved in a direction that is parallel or substantially parallel to the sagittal plane 202 of the person 204 (e.g., within ten degrees of parallel, within 15 degrees of parallel, etc.). As the ultrasound probe 106 is moved in this direction during acquisition of ultrasound image data, the ultrasound probe 106 moves transversely or substantially transversely to directions in which the plurality of ribs are elongated.

Figure 3:
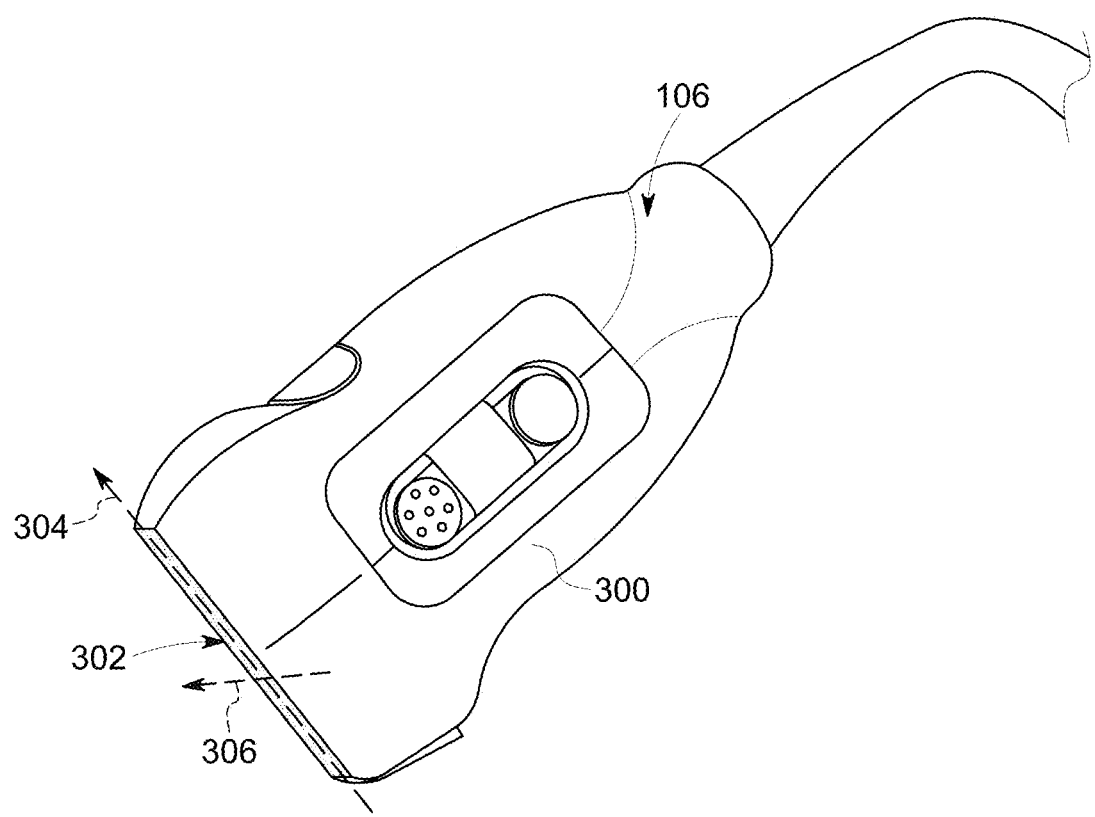
FIG. 3 illustrates an ultrasound probe in accordance with an embodiment.

FIG. 3 illustrates one embodiment of the ultrasound probe 106 of the ultrasound imaging system 100 shown in FIG. 1. The ultrasound probe 106 can have a housing 300 that holds the elements 104 (not visible inside the housing 300 in FIG. 3). The housing 300 of the ultrasound probe 106 interfaces (e.g., contacts) the person 204 along a face surface 302 of the housing 300. This face surface 302 is elongated along a first direction 304 relative to an orthogonal (e.g., perpendicular) direction 306.

The ultrasound probe 106 can be moved along the outside of the person 204 along the thoracic cavity 200 to acquire ultrasound image data of the lungs 208 of the person 204. In one embodiment, the ultrasound probe 106 is moved transversely to directions in which the plurality of ribs are elongated. For example, the ultrasound probe 106 can be moved along the exterior of the person 204 in directions that are more parallel to the sagittal plane 202 than perpendicular to the sagittal plane 202.

The ultrasound probe 106 can be held in an orientation that has the elongated direction 304 of the housing 300 of the ultrasound probe 106 oriented parallel (or more parallel than perpendicular) to the plurality of ribs of the person 204 while the ultrasound probe 106 is moved along a direction substantially parallel to the sagittal plane 202. This orientation of the ultrasound probe 106 can be referred to as a sagittal position or orientation of the ultrasound probe 106. Alternatively, the ultrasound probe 106 can be held in an orientation that is perpendicular to the sagittal orientation. This orientation results in the ultrasound probe 106 being oriented such that the elongated direction 304 of the housing 300 of the probe 106 is perpendicular to (or more perpendicular than parallel) the plurality of ribs of the person 204 while the probe 106 is moved along in a direction substantially parallel to the sagittal plane 202. This orientation of the probe 106 can be referred to as a transverse position or orientation of the probe 106.

Figure 4:
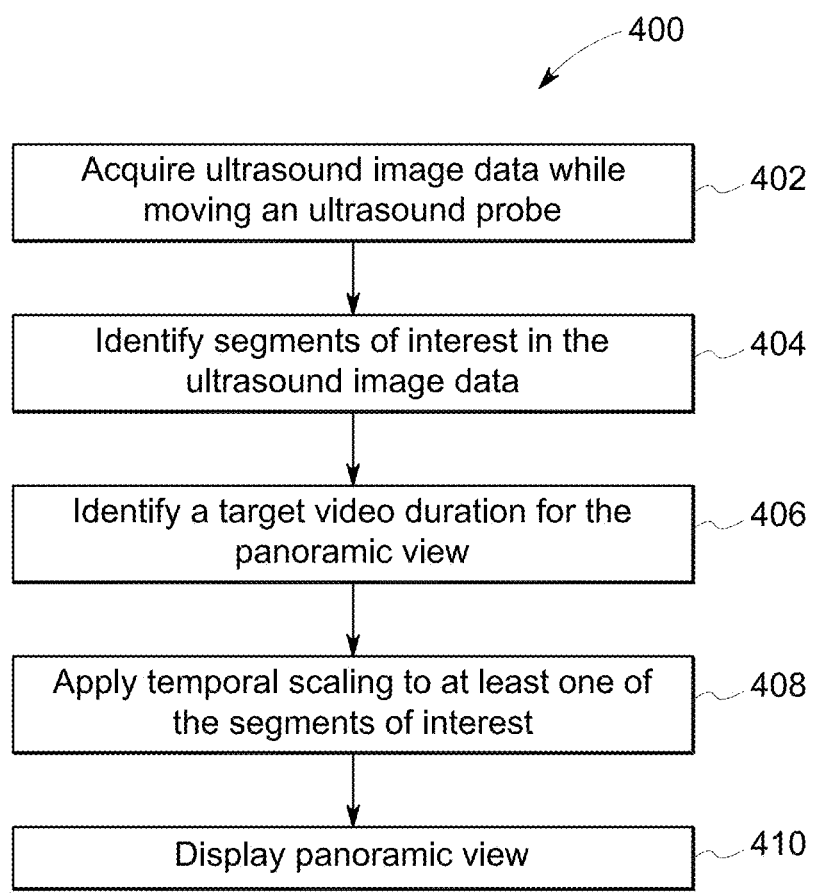
FIG. 4 illustrates a flowchart of an embodiment of a method in accordance with an embodiment.

FIG. 4 illustrates a flowchart of one embodiment of a method 400 for acquiring ultrasound image data and displaying a panoramic image based on the ultrasound image data. The technical effect of the method 400 is to acquire ultrasound image data of a body (e.g., a lung or another body part) and to display a panoramic view showing a plurality of temporally scaled videos of the ultrasound image data. The method 400 will be described with respect to an embodiment where the ultrasound image data is acquired of the person's lung, but it should be appreciated that the method may be used to acquire different anatomical regions according to other embodiments.

At step 402, ultrasound image data is acquired while the ultrasound probe 106 is moved. In obtaining the ultrasound image data, the ultrasound probe 106 may be held in contact with an exterior surface of the skin of the person 204 and moved transversely to the person's ribs. For example, the ultrasound probe 106 may be moved in a direction that is parallel or substantially parallel to the sagittal plane 202 of the person 204 (e.g., within ten degrees of parallel, within 15 degrees of parallel, etc.). As the ultrasound probe 106 is moved in this direction during acquisition of ultrasound image data, the ultrasound probe 106 moves transversely or substantially transversely to the direction in which the various ribs are elongated. Alternatively, the ultrasound probe 106 may be moved in directions that are parallel to the direction in which the ribs are elongated. According to other embodiments, the ultrasound probe 106 may be moved in directions other than parallel to the direction in which the ribs are elongated or substantially transverse to the direction in which the ribs are elongated. The ultrasound image data may, for example, include a plurality of image frames acquired as the ultrasound probe 106 is moved along the body. Each of the plurality of image frames represents ultrasound image data acquired at a unique point in time. And, since the ultrasound probe 106 is being moved along the body during the acquisition of the ultrasound image data at step 402, each of the image frames may be acquired from a slightly different position on the patient's body as well.

In one embodiment, the ultrasound image data is acquired while the ultrasound probe 106 is held in the same orientation (e.g., only the sagittal orientation or only the transverse orientation) and moved in a single direction (e.g., only toward the head of the person 204 or only away from the head of the person 204). In another embodiment, the ultrasound image data is acquired while the ultrasound probe 106 is held in different orientations (e.g., part of the ultrasound image data is acquired while the probe 106 is held in the sagittal orientation, and another part of the ultrasound image data is acquired while the probe 106 is held in the transverse orientation) and moved in a single direction. In another embodiment, the ultrasound image data is acquired while the ultrasound probe 106 is held in the same or different orientations and moved in two or more different directions (e.g., opposite directions, transverse directions, orthogonal directions, etc.).

Figure 5A:
FIG. 5A illustrates one example of ultrasound image data of a lung and ribs.

FIG. 5A illustrates one example of ultrasound image data 500 of the lung 208 and ribs of the person 204 acquired with the ultrasound probe 106 held in a sagittal orientation. FIG. 5A includes a plurality of segments of interest and a plurality of rib shadows. The rib shadows indicate locations where passage of the pulsed ultrasonic signals was blocked by the ribs. For example, FIG. 5A includes a first segment of interest 531, a second segment of interest 532, a third segment of interest 533, and a fourth segment of interest 534. FIG. 5 also includes a second rib shadow 522, a third rib shadow 523, and a fourth rib shadow 524. The second rib shadow 522 is caused by the second rib 222; the third rib shadow 523 is caused by the third rib 223; and the fourth rib shadow 524 is caused by the fourth rib 224.

In one embodiment, the processor 116 may be configured to automatically identify segments of interest in the ultrasound image data. A segment of interest can be a subset or portion of the combined image data that is selected based on characteristics of the image data. The processor 116 can examine characteristics of the pixels (or other subsets of the image data) to identify the segments of interest, such as the color, intensity, brightness, or the like, of the pixels in the image data.

The image data 500 may be a video showing movement of one or more portions of the intercostal spaces 504 and/or rib shadows 506. This movement can result in one or more features of interest appearing at times and disappearing from the ultrasound image data 500 at other times. For example, B-lines or other features in the image data 500 that indicate pneumonia infection, air bronchograms, or other damage may be visible in some, but not all, of the image frames.

The processor 116 can examine the image data acquired by the ultrasound probe 106 to determine how quickly the probe 106 is moving relative to the body of the person 204. For example, as new or additional ultrasound image data is acquired of new or different areas of the lung 208, ribs, or the like, the processor 116 can determine that the ultrasound probe 106 is being moved. These new or different areas can include image data of additional intercostal spaces and/or rib shadows. Returning to the description of the flowchart of the method 400 shown in FIG. 4, after the acquisition of the ultrasound data, such as during a sweep of the ultrasound probe 106, the method 400 advances to step 404. According to some embodiments, the clinician may indicate that all the ultrasound image data for the panoramic image has been acquired through an input through the user interface 115. According to some embodiments, the clinician may actuate a button, such as a freeze button in order to indicate the acquisition of the ultrasound data has been completed. At step 404, the processor 116 identifies segments of interest in the ultrasound image data. According to an exemplary embodiment, it may be desirable to identify segments of interest corresponding to the intercostal spaces, such as the first intercostal space 231, the second intercostal space 232, the third intercostal space 233, the fourth intercostal space 234, and the fifth intercostal space 235. The processor 116 can identify the segments of interest, such as the intercostal spaces, based on changes in the characteristics of the image data, such as changes in intensity (e.g., increasing in intensity when an additional intercostal space is being imaged or decreasing in brightness when a rib is being imaged. An exemplary embodiment showing how the processor 116 may use intensity information in the ultrasound image data to identify the segments of interest will be described with respect to FIG. 5B.

Figure 5B:
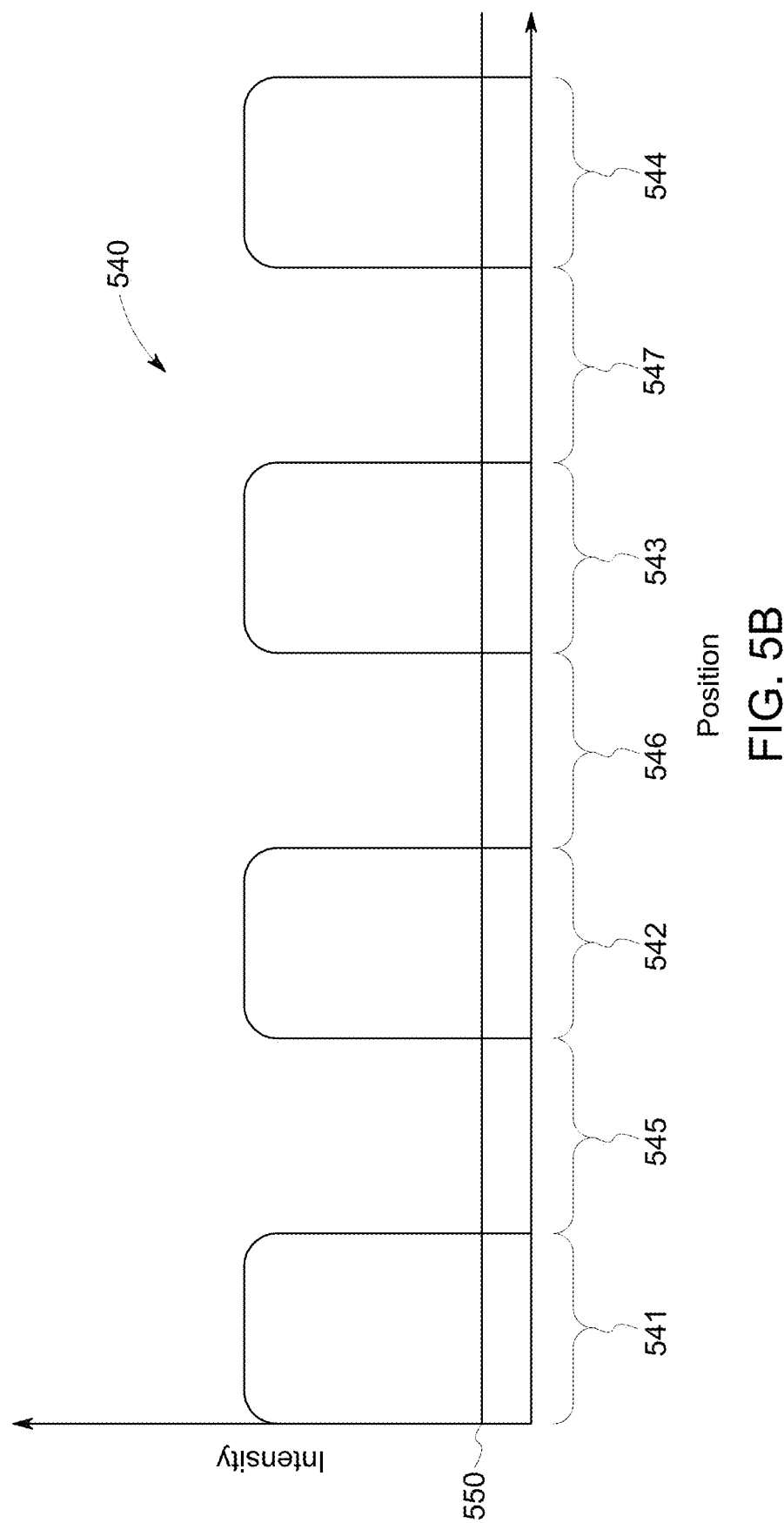
FIG. 5B is a graph showing intensity versus time according to an embodiment.

FIG. 5B is a graph 540 showing intensity versus position for the ultrasound image data used to generate the image 500 shown in FIG. 5A. The graph 540 includes a first portion 541, a second portion 542, a third portion 543, a fourth portion 544, a fifth portion 545, a sixth portion 546, and a seventh portion 547. The first portion 541 represents the portion of the ultrasound image data acquired from the first intercostal region 231 and shown on the image 500 as the first segment of interest 531; the second portion 542 represents the portion of the ultrasound image data acquired from the second intercostal region 232 and shown on the image 500 as the second segment of interest 532; the third portion 543 represents the portion of the ultrasound image data acquired from the third intercostal region 233 and shown on the image 500 as the third segment of interest 533; and the fourth portion 544 represents the portion of the ultrasound image data acquired from the fourth intercostal region 234 and shown on the image 500 as the fourth segment of interest 534. The fifth portion 545 represents the second rib shadow 522; the sixth portion 546 represents the third rib shadow 523; and the seventh portion 547 represents the fourth rib shadow 524.

FIG. 5B illustrates the differences between the portions of the ultrasound image data acquired from intercostal spaces and the portions of the ultrasound image data acquired from regions including a rib (i.e., the portions that would be represented as a rib shadow in an image). The portions of the ultrasound image data acquired from intercostal spaces have a much higher intensity than the ultrasound image data acquired from regions obscured by a rib. The presence of a rib blocks all or almost all of the acoustic energy and results in an intensity of either zero or close-to zero. On the image 500, the portions of the ultrasound image data including a rib are depicted as rib shadows, such as the second rib shadow 522, the third rib shadow 523, and the fourth rib shadow 524.

According to an embodiment, the processor 116 may identify the segments of interest based on the intensity of the ultrasound image data. For example, the processor 116 may compare the ultrasound image data to a threshold: if the ultrasound image data is above a threshold, the ultrasound image data is of a segment of interest; if the ultrasound image data is below the threshold, the ultrasound image data represents a rib shadow and does not include a segment of interest. An exemplary threshold 550 is shown on FIG. 5B. According to embodiments, the processor 116 may use other image properties to identify the segments of interest from the ultrasound image data. For example, the processor 116 may use information such as Doppler data, speckle tracking, or colorflow data to identify the segments of interest within the ultrasound image data. The processor 116 may also use artificial intelligence, such as by using a neural network to identify the segments of interest in the ultrasound image data.

Figure 5C:
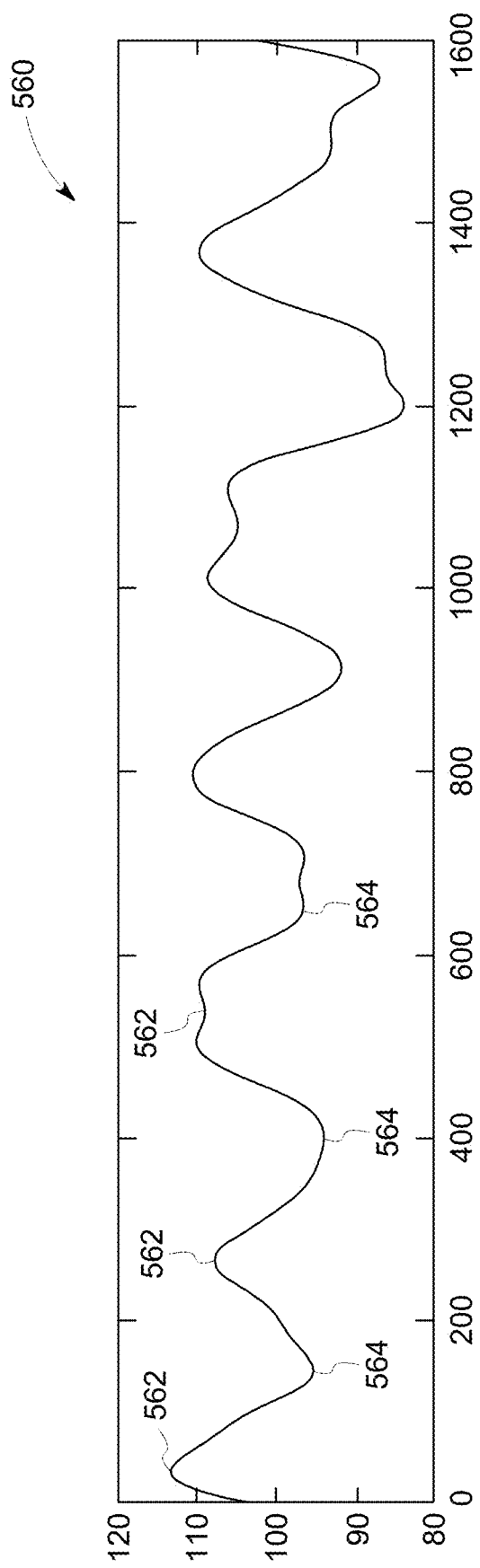
FIG. 5C is a plot of Center of Mass versus time according to an embodiment.

According to another embodiment, the processor 116 may use a center-of-mass (COM) calculation where pixel intensity in the image is treated as the equivalent of mass. The processor 116 may calculate the vertical position of the COM at each location in the direction of the translation or sweep of the ultrasound probe 106. At locations where there is a rib and a rib shadow, the COM tends to be close to the surface of the ultrasound probe 106 (i.e., at shallower depths in the image), while the COM tends to be deeper for portions of the image with an intercostal space. The processor 116 may determine the positions of rib shadows and intercostal spaces based on the COM calculation with respect to either time or distance. For example, according to an exemplary embodiment, the processor 116 may identify positions of ribs and rib shadow by identifying regions of the image where the COM calculation is relatively high; and the processor 116 may identify positions of intercostal spaces or pleural regions in the image by identifying regions of the image where the COM calculations are relatively low. For example, FIG. 5C shows an example of a COM plot 560. The COM plot 560 shows the vertical position of the COM with respect to horizontal position in the image. The processor 116 may identify the relative peaks 562 in the COM plot 560 and the relative valleys 564 in the COM plot 560. The relative peaks 562 correspond to regions of the image with ribs and rib shadows whereas the relative valleys 564 correspond to regions of the image obtains from intercostal spaces/pleural regions.

At step 406, the processor 116 identifies a target video duration to be used with a panoramic view. According to an embodiment, the processor 116 may determine an acquisition duration for each of the segments of interest in the ultrasound image data and use the acquisition durations in order to determine the target video duration. According to an embodiment, the processor 116 may use the intensity information from the ultrasound image data, such as intensity information represented in FIG. 5B, or according to the COM calculation such as that represented in FIG. 5C, to identify a start time and an end time for each of the segments of interests. According to an embodiment, the segments of interest correspond to the intercostal spaces and show data acquired from the person's lung. As was described with respect to step 402, the ultrasound probe 106 is moved with respect to the person as the ultrasound image data is acquired. For example, the ultrasound probe 106 may be translated in a direction substantially parallel to the sagital plane 202 in order to acquire the ultrasound image data. The ultrasound image data includes a plurality of frames of ultrasound image data, each acquired at a different time. As long as the ultrasound probe 106 is being translated during the acquisition of the ultrasound image data, each of the image frames will be acquired from a different spatial position with respect to the person's anatomy. According to one embodiment, the processor 116 may use the intensity information in order to identify the start time and the end time associated with each of the segments of interest. The processor 116 may be configured to identify the times associated with the transition from rib shadow to intercostal space and the transition from the intercostal space to rib shadow. For instance, as shown in FIG. 5B, the intensities associated with the rib shadows are very low, and the intensities associated with the intercostal spaces are much higher. As the probe is being translated during the acquisition of the ultrasound data during step 402, the anatomy being acquired in each frame of the ultrasound image data is different. The processor 116 may be configured to identify the frame in the ultrasound image data where the ultrasound image data first transitions from the relatively low intensity associated with a rib shadow to the relatively high intensity associated with a particular intercostal space. Likewise, the processor 116 may be configured to identify the frame in the ultrasound image data where the ultrasound image data transitions from a particular intercostal space with a relatively high intensity to the adjacent (next) rib shadow with a relatively low intensity.

According to another embodiment, the processor 116 may use information from the COM calculation in order to determine the acquisition duration of each of the segments of interest in the ultrasound image data. For example, the processor 116 may identify the rib and/or rib shadow locations using a COM calculation as was described previously with respect to FIG. 5C. Once the locations of the ribs and/or rib shadows are determined, the processor 116 may use this information to determine the acquisition time of the first frame including a specific intercostal space and the acquisition time of the last frame including the specific intercostal space. The processor 116 may use the COM information to identify the frames in the ultrasound data covering each of the segments of interest.

Each of the frames identified by the processor 116 may have a time stamp indicating the time of acquisition. The processor 116 may use the identified frames and/or the associated time stamps, to identify the start time and the end time for each of the segments of interest, which are intercostal spaces according to an exemplary embodiment. Based on identified start time and the end time for each of the segments of interest in the ultrasound image data, the processor 116 may calculate an acquisition duration for each of the segments of interest by, for example, calculating the amount of time between the start time and the end time for each segment of interest (e.g., for each intercostal region).

According to other embodiments, the processor 116 may rely on a fixed, or predetermined target video duration. The processor 116 may, for instance, apply temporal scaling to all or at least some of the segments of interest so that videos based on the segments of interest will each be of the target video duration. This results in a panoramic view where each of the videos takes the same amount of time to play. In other words, after being temporally scaled, each of the videos in the panoramic view will be of the target video duration.

At step 408, the processor 116 applies temporal scaling to one or more of the segments of interest. The processor 116 may temporally scale the ultrasound image data by expanding one or more of the segments of interest and/or contracting one or more of the segment of interest. For example, the processor 116 may temporally scale the segment of interest by temporally expanding the ultrasound image data in the segment of interest so the video takes a longer amount of time to play. Or, the processor 116 may temporally scale the segment of interest by contracting the ultrasound image data in the segment of interest so the video takes a shorter amount of time to play. Temporally expanding the segment of interest results in the associated video playing at a slower frame-rate than acquisition frame-rate; and temporally contracting the segment of interest results in the associated video playing at a faster frame-rate than the acquisition frame-rate.

The processor 116 may utilize additional techniques either in addition to or in place of temporally contracting or expanding the ultrasound image data in order to perform the temporal scaling of one or more segments of interest. For example, the processor 116 may temporally expand some of the segments of interest while temporally contracting other segments of interest. If the ultrasound image data associated with a particular segment of interest has significantly fewer frames than ultrasound image data associated with other segments of interest, the processor 116 may play the video with fewer frames more than one time while the video with a larger number of frames is played only a single time. For example, if a first segment of interest has 10 frames and second segment of interest has 30 frames, the processor 116 may play a first video based on the first segment of interest three times, while a second video based on the second segment of interest is only played a single time in order to provide appropriate temporal scaling of the first segment of interest and the second segment of interest.

According to another embodiment, the processor 116 may generate one or more interpolated frames in order to ensure that playback of each of the videos in the panoramic image takes the same amount of time. For example, the processor 116 may insert interpolated frames in order to adjust the time it takes for the video based on the particular segment of interest to play. For example, the processor 116 may add interpolated frames to a segment of interest that is shorter than desired in order to provide appropriate temporal scaling of the ultrasound image data so all of the videos take the same amount of time to play. The processor 116 may be configured to use a combination of the techniques described hereinabove in order to provide the temporal scaling. For example, the processor 116 may be configured to use two or more of the following techniques: temporally expanding, temporally contracting, playing videos of a segment of interest more than one time, or adding interpolated frames to the video associated with a segment of interest. According to other embodiments, temporal scaling may include a relative temporal scaling. For example, the processor 116 may play back each of the videos at a speed other than that at which the ultrasound image data was acquired. The processor 116 may therefore provide a relative temporal scaling between the videos based on how much the playback speed for each of the videos is adjusted in relation to the other videos in the panoramic view. In other words, the temporal scaling is performed by adjusting the relative playback speeds of each of the videos in the panoramic view.

According to another embodiment, applying the temporal scaling to a segment of interest may include repeating one or more of the frames of the segment of interest when displaying a video based on the segment of interest. For example, by repeating one or more of the frames in the video, the video may be temporally scaled to take more time to play, assuming the video is played at the same frame rate.

A segment of interest may be temporally scaled in order to achieve a target video duration. The target video duration may be based on the length of one or more of the segments of interest, the target video duration may be selected by the clinician, or the target video duration may be a predetermined length of time. For example, the ultrasound image data associated with one or more segments of interest may be temporally scaled to match the length of video associated with a particular segment of interest. According to an embodiment, the processor 116 may be configured to apply temporal scaling to the ultrasound image data so each of the videos in the panoramic view takes the same amount of time to play. According to an embodiment, the processor 116 may temporally scale the ultrasound image data so each of the videos takes the same amount of time to play as a longest one of the videos. According to an embodiment, the processor 116 may temporally scale the ultrasound image data associated with one or more segments of interest so each of the videos takes the same amount of time to play as a shortest one of the videos. Additional details about temporally scaling the ultrasound image data will be discussed hereinafter. At step 410, the processor 116 displays the ultrasound image data in a panoramic view, such as panoramic view 600, shown in FIG. 6. Additional details about the panoramic view 600 will be provided hereinafter.

As described previously, a panoramic view can be acquired by obtaining different portions of the ultrasound image data as the probe 106 is moved over the person 204, and then stitching or otherwise combining these different ultrasound image data portions together to form the panoramic view. The processor 116 may use image information, such as brightness values, shape/pattern identification, or other matching algorithms to combine the portions of the ultrasound image data associated with various segments of interest in the panoramic view 600.

The panoramic view 600 of the ultrasound image data can show or include more image data of the patient than the ultrasound probe 106 can obtain in a single field-of-view (FOV). For example, the FOV of the ultrasound probe 106 may be much smaller than the panoramic view 600.

Figure 6:
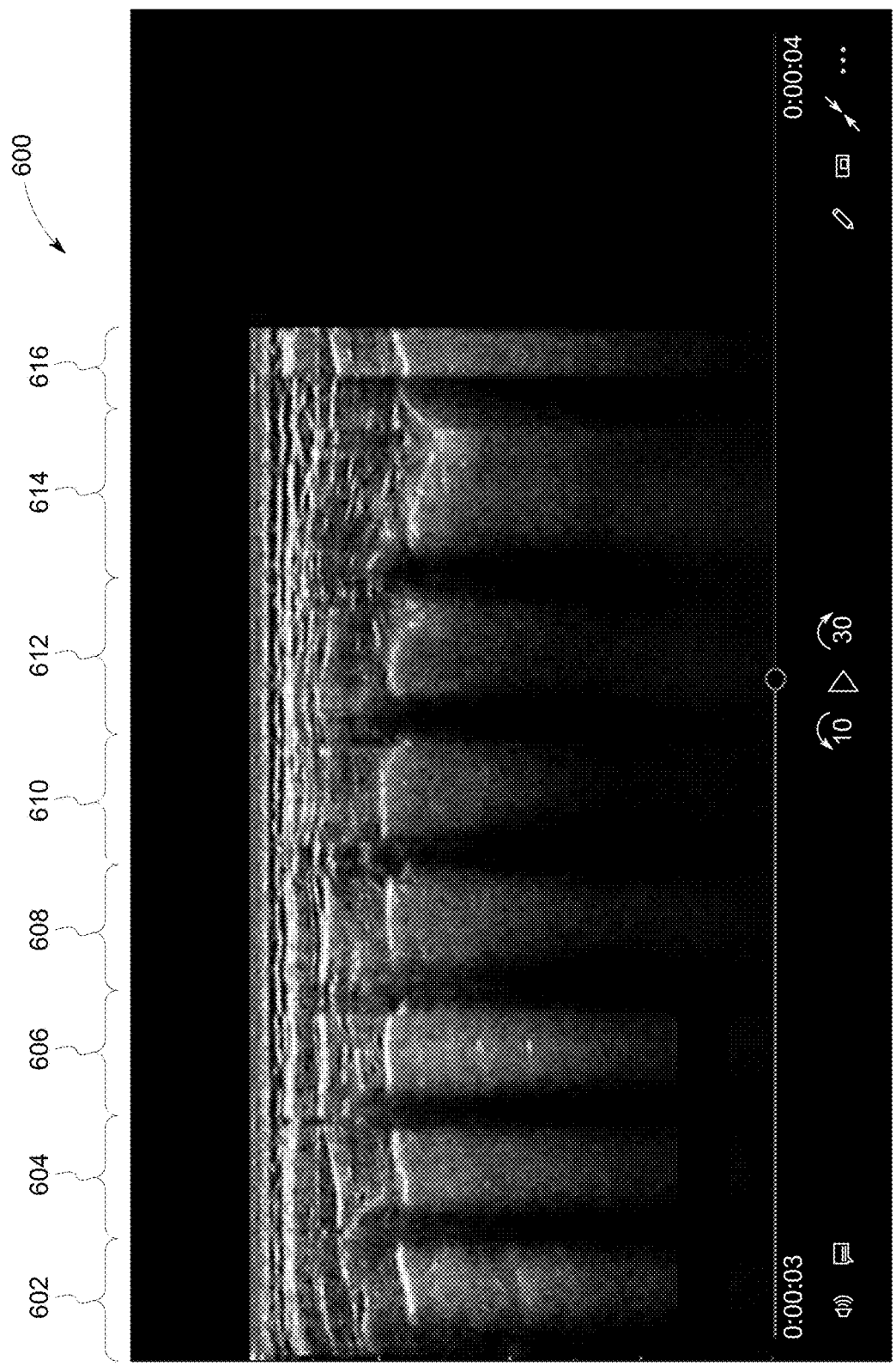
FIG. 6 is an illustration of a panoramic image according to an embodiment.

Referring to FIG. 6, the panoramic view 600 includes a first portion 602, a second portion 604, a third portion 606, a fourth portion 608, a fifth portion 610, a sixth portion 612, a seventh portion 614, and an eighth portion 616. A video based on a different segment of interest is displayed in each of the portions of the panoramic view 600. For example, a first video based on a first segment of interest may be displayed in the first portion 602; a second video based on a second segment of interest may be displayed in the second portion 604; a third video based on a third segment of interest may be displayed in the third portion 606; a fourth video based on a fourth segment of interest may be displayed in the fourth portion 608; a fifth video based on a fifth segment of interest may be displayed in the fifth portion 610; a sixth video based on a sixth segment of interest may be displayed in the sixth portion 612; a seventh video based on a seventh segment of interest may be displayed in the seventh portion 614; and an eighth video based on an eight segment of interest may be shown in the eighth portion 616. According to the embodiment shown in FIG. 6, each of the segments of interest may be ultrasound image data acquired from a different intercostal space of a patient's lung region.

According to an embodiment, displaying each of the plurality of videos in the panoramic view may include displaying each of the plurality of videos as a repeating loop, or cine loop. When displayed as a repeating loop, each video is continuously replayed. In other words, each video transitions from the last frame in the video to the first frame in video when displayed as a repeating loop. Temporally scaling the ultrasound image data refers to adjusting the length of time it takes each video to play before looping or repeating. The length of time it takes for each video to play in a panoramic view may also be referred to as a period of the repeating loop. Temporally scaling may be used so that each of the videos displayed as a repeating loop in the panoramic view has the same period.

Temporally scaling the ultrasound image data enables the display of a panoramic view, such as the panoramic view 600, where each of the video takes the same amount of time to play before repeating. The processor 116 may also synchronize all the videos in the panoramic view so each of the videos transitions from an end of the loop to a start of the loop (i.e., loops) at the same time. A panoramic view including videos that have been temporally scaled and synchronized results in fewer distractions for a user. This allows the clinician to focus on the diagnostically important aspects of the panoramic view instead of being distracted by the discontinuities caused by videos looping at different points in time.

By automatically performing temporal scaling on the ultrasound image data, the processor 116 is able to present a panoramic view to the clinician where each video is the same length without any additional user input. Performing the temporal scaling additionally has the advantage of presenting a panoramic video that is easier for the clinician to view and interpret because it is less visually distracting to the clinician.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of ultrasound imaging comprising:
   acquiring ultrasound image data while moving an ultrasound probe;
   automatically identifying a plurality of segments of interest in the ultrasound image data;
   automatically applying temporal scaling to at least one of the plurality of segments of interest; and
   displaying the ultrasound image data as a panoramic view comprising a plurality of videos, wherein each of the plurality of videos is based on a different one of the plurality of segments of interest, and wherein, based on the temporal scaling, each of the plurality of videos in the panoramic view takes the same amount of time to play.

2. The method of claim 1, wherein the temporal scaling comprises at least one of: expanding one of the plurality of segments of interest; contracting one of the plurality of segments of interest; playing one of the plurality of videos more than one time to achieve a target video duration; performing a relative temporal scaling between two of the plurality of segments of interest; or generating a plurality of interpolated frames and inserting the plurality of interpolated frames into one of the plurality of videos to achieve the target video duration.

3. The method of claim 1, wherein the temporal scaling comprises expanding one of the plurality of segments of interest.

4. The method of claim 1, wherein the temporal scaling comprises contracting one of the plurality of segments of interest.

5. The method of claim 1, wherein the temporal scaling comprises playing one of the plurality of videos more than one time to achieve a target video duration.

6. The method of claim 1, wherein the temporal scaling comprises performing a relative temporal scaling between two of the plurality of segments of interest.

7. The method of claim 1, wherein the temporal scaling comprises generating a plurality of interpolated frames and inserting the plurality of interpolated frames into one of the plurality of videos to achieve a target video duration.

8. The method of claim 1, wherein the ultrasound image data is acquired of a lung and includes both a plurality of rib shadows and a plurality of intercostal spaces, wherein each of the plurality of segments of interest represents one of the plurality of intercostal spaces.

9. The method of claim 8, wherein each of the plurality of intercostal spaces is determined by identifying one of the following: at least one of the plurality of rib shadows in the ultrasound image data; at least one of the plurality of intercostal spaces in the ultrasound image data; both at least one of the plurality of rib shadows and at least one of the plurality of intercostal spaces in the ultrasound image data.

10. The method of claim 8, wherein each of the plurality of intercostal spaces is identified in the ultrasound image data by using a center-of-mass calculation where image intensity is treated as an equivalent of mass.

11. An ultrasound imaging system comprising:
    a display device;
    an ultrasound probe configured to acquire ultrasound image data; and
    a processor in electronic communication with the ultrasound probe and the display device, wherein the processor is configured to:
    automatically identifying a plurality of segments of interest in the ultrasound image data;
    automatically apply temporal scaling to at least one of the plurality of segments of interest; and
    display, on the display device, the ultrasound image data as a panoramic view comprising a plurality of videos, wherein each of the plurality of videos is based on a different one of the plurality of segments of interest, and wherein, based on the temporal scaling, each of the plurality of videos in the panoramic view takes the same amount of time to play.

12. The ultrasound imaging system of claim 11, wherein the temporal scaling comprises at least one of: expanding one of the plurality of segments of interest; contracting one of the plurality of segments of interest; playing one of the plurality of videos more than one time to achieve a target video duration; performing a relative temporal scaling between two of the plurality of segments of interest; or generating a plurality of interpolated frames and inserting the plurality of interpolated frames into one of the plurality of videos to achieve the target video duration.

13. The ultrasound imaging system of claim 11, wherein the temporal scaling comprises expanding one of the plurality of segments of interest.

14. The ultrasound imaging system of claim 11, wherein the temporal scaling comprises contracting one of the plurality of segments of interest.

15. The ultrasound imaging system of claim 11, wherein the temporal scaling comprises playing one of the plurality of videos more than one time to achieve a target video duration.

16. The ultrasound imaging system of claim 11, wherein the temporal scaling comprises performing a relative temporal scaling between two of the plurality of segments of interest.

17. The ultrasound imaging system of claim 11, wherein the temporal scaling comprises generating a plurality of interpolated frames and inserting the plurality of interpolated frames into one of the plurality of videos to achieve a target video duration.

18. The ultrasound imaging system of claim 11, wherein the ultrasound image data is acquired of a lung and includes both a plurality of rib shadows and a plurality of intercostal spaces, wherein each of the plurality of segments of interest represents one of the plurality of intercostal spaces.

19. The ultrasound imaging system of claim 11, wherein each of the plurality of intercostal spaces is determined by identifying one of the following: at least one of the plurality of rib shadows in the ultrasound image data; at least one of the plurality of intercostal spaces in the ultrasound image data; both at least one of the plurality of rib shadows and at least one of the plurality of intercostal spaces in the ultrasound image data.

20. The ultrasound imaging system of claim 11, wherein each of the plurality of intercostal spaces is identified in the ultrasound image data by using a center-of-mass calculation where image intensity is treated as an equivalent of mass.

* * * * *